United States Patent
Tokunaga et al.

(10) Patent No.: US 10,844,010 B2
(45) Date of Patent: Nov. 24, 2020

(54) PROCESS FOR PRODUCING (POLY)SULFIDE COMPOUND AND PROCESS FOR PRODUCING EPISULFIDE COMPOUND

(71) Applicant: MITSUI CHEMICALS, INC., Tokyo (JP)

(72) Inventors: Koichi Tokunaga, Chikugo (JP); Chitoshi Shimakawa, Arao (JP); Shigetoshi Kuma, Kurume (JP); Masaru Kawaguchi, Omuta (JP)

(73) Assignee: MITSUI CHEMICALS, INC., Tokyo (JP)

( * ) Notice: Subject to any disclaimer, the term of this patent is extended or adjusted under 35 U.S.C. 154(b) by 0 days.

(21) Appl. No.: 16/084,632

(22) PCT Filed: Mar. 17, 2017

(86) PCT No.: PCT/JP2017/010845
§ 371 (c)(1),
(2) Date: Sep. 13, 2018

(87) PCT Pub. No.: WO2017/159839
PCT Pub. Date: Sep. 21, 2017

(65) Prior Publication Data
US 2019/0077751 A1 Mar. 14, 2019

(30) Foreign Application Priority Data
Mar. 18, 2016 (JP) .................. 2016-054906

(51) Int. Cl.
| | |
|---|---|
| *C07C 319/14* | (2006.01) |
| *C07D 331/02* | (2006.01) |
| *C07C 319/24* | (2006.01) |
| *C08G 75/14* | (2006.01) |
| *C07B 61/00* | (2006.01) |
| *G02B 1/04* | (2006.01) |

(52) U.S. Cl.
CPC .......... *C07C 319/14* (2013.01); *C07C 319/24* (2013.01); *C07D 331/02* (2013.01); *C08G 75/14* (2013.01); *C07B 61/00* (2013.01); *C08L 2203/00* (2013.01); *G02B 1/041* (2013.01)

(58) Field of Classification Search
CPC ... C07C 319/14; C07C 319/24; C07D 319/24; C07B 61/00; G02B 1/04; C08L 81/00; C08L 2203/00; B29B 13/00; B30B 9/28; C08G 75/14; C08G 75/08
USPC ...................................... 528/375
See application file for complete search history.

(56) References Cited

U.S. PATENT DOCUMENTS

| | | | |
|---|---|---|---|
| 6,204,311 B1 | 3/2001 | Morijiri et al. | |
| 6,300,464 B2 | 10/2001 | Morijiri et al. | |
| 6,458,917 B2 | 10/2002 | Morijiri et al. | |
| 6,686,506 B1 | 2/2004 | Hesse et al. | |
| 9,242,947 B2 | 1/2016 | Aoki et al. | |
| 9,458,293 B2 | 10/2016 | Aoki et al. | |
| 10,266,636 B2 | 4/2019 | Tsukada et al. | |
| 2001/0002413 A1 | 5/2001 | Morijiri et al. | |
| 2002/0019511 A1 | 2/2002 | Morijiri et al. | |
| 2014/0371475 A1 | 12/2014 | Aoki et al. | |
| 2014/0378628 A1 | 12/2014 | Aoki et al. | |
| 2017/0015776 A1 | 1/2017 | Tsukada et al. | |
| 2017/0015777 A1 | 1/2017 | Tsukada et al. | |

FOREIGN PATENT DOCUMENTS

| | | |
|---|---|---|
| JP | 2000-186086 A | 7/2000 |
| JP | 2000-186087 A | 7/2000 |
| JP | 2000256435 A | 9/2000 |

(Continued)

OTHER PUBLICATIONS

Office Action dated Jul. 4, 2018, by the Japanese Patent Office in Japanese Patent Application No. 2017-526151 (2 pages).

(Continued)

*Primary Examiner* — Shane Fang
(74) *Attorney, Agent, or Firm* — Buchanan Ingersoll & Rooney PC

(57) ABSTRACT

In a process for producing a (poly) sulfide compound represented by General Formula (2) of the present invention, thiol compounds represented by General Formula (1) are reacted with each other in the presence of a basic compound represented by General Formula (4) or General Formula (5) and sulfur.

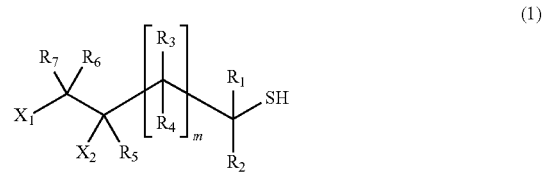

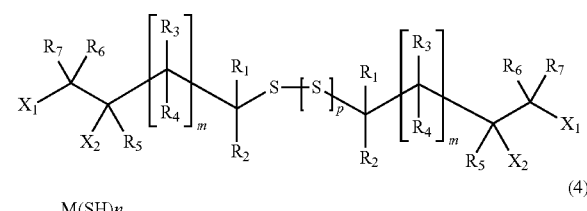

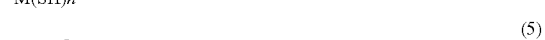

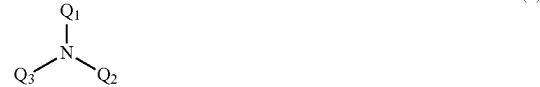

8 Claims, No Drawings

(56) References Cited

FOREIGN PATENT DOCUMENTS

| JP | 2001-163874 | A  | 6/2001  |
|----|-------------|----|---------|
| JP | 2002194083  | A  | 7/2002  |
| JP | 2002530371  | A  | 9/2002  |
| JP | 2007091652  | A  | 4/2007  |
| JP | 2013142073  | A  | 7/2013  |
| WO | 2013115212  | A1 | 8/2013  |
| WO | 2013157490  | A1 | 10/2013 |
| WO | 2015137402  | A1 | 9/2015  |

OTHER PUBLICATIONS

International Search Report (PCT/ISA/210) dated Apr. 25, 2017, by the Japanese Patent Office as the International Searching Authority for International Application No. PCT/JP2017/010845.
Written Opinion (PCT/ISA/237) dated Apr. 25, 2017, by the Japanese Patent Office as the International Searching Authority for International Application No. PCT/JP2017/010845.
Office Action dated Apr. 22, 2020, by the State Intellectual Property Office of the Peoples Republic of China in corresponding Chinese Patent Application No. 201780016235.1. (5 pages).

PROCESS FOR PRODUCING (POLY)SULFIDE COMPOUND AND PROCESS FOR PRODUCING EPISULFIDE COMPOUND

TECHNICAL FIELD

The present invention relates to a process for producing a (poly)sulfide compound having a bishalohydrin group and a process for producing an episulfide compound having a (poly)sulfide bond.

BACKGROUND ART

Compared with inorganic lenses, plastic lenses have a low weight, are not easily cracked, and can be dyed, and thus, recently, have rapidly become widespread in optical elements such as eyeglass lenses and camera lenses.

For resins for plastic lenses, there has been a demand for additional improvement in performance, and there has been a demand for an increase in the refractive index, an increase in the Abbe number, a decrease in the specific weight, an improvement of the heat resistance, and the like. Thus far, a variety of resin materials for lenses have been developed and put into use.

Among them, optical materials comprised of sulfide-based resins have a high refractive index and a high Abbe number and are being studied as ultrahigh refractive index materials having a refractive index of higher than 1.6. Sulfide-based resins are obtained by polymerizing a polymerizable composition including an episulfide compound.

For molded product comprised of a sulfide-based resin, for the purpose of increasing the refractive index, a method for improving the content ratio of sulfur in a resin is proposed. For the above-described purpose, an episulfide compound having a disulfide bond (—S—S—) is used (Patent Documents 1 to 3). Patent Document 1 describes that, when an episulfide compound having one or more disulfide bonds in the molecule and two or more 2,3-epithiopropyl groups in the molecule is used as a monomer, a sulfide-based resin having a refractive index of more than 1.71 is obtained.

Patent Documents 1 and 4 to 8 disclose process for producing an episulfide compound, and Patent Documents 1 and 6 to 8 disclose methods for synthesizing an episulfide compound having a disulfide bond using an oxidation reaction of a thiol.

In Synthesis Example 1 of Patent Document 1, it is described that chloromercaptopropanol is reacted in the presence of sodium hydrogen carbonate and iodine and then reacted in the presence of caustic soda, thereby obtaining bis(2,3-epoxypropyl)disulfide.

In Example 5 of Patent Document 6 or Examples 5 and 6 of Patent Document 7, it is described that chloromercaptopropanol is reacted in the presence of sodium hydrogen carbonate and iodine, thereby obtaining a disulfide body.

In Patent Document 8, a process for producing a polythiol oligomer having a disulfide bond by reacting a polythiol compound and sulfur in the presence of a basic catalyst is proposed. In Example 1, it is described that, specifically, 2,5-dimercaptomethyl-1,4-dithiane is reacted in the presence of sulfur and triethylamine which is a basic catalyst, thereby obtaining an oligomer (a disulfide body or the like) of the compound.

RELATED DOCUMENT

Patent Document

[Patent Document 1] Japanese Unexamined Patent Publication No. 2002-194083
[Patent Document 2] Japanese Unexamined Patent Publication No. 2000-256435
[Patent Document 3] International Publication No. WO2013/115212
[Patent Document 4] Japanese Unexamined Patent Publication No. 2001-163874
[Patent Document 5] International Publication No. WO2013/157490
[Patent Document 6] Japanese Unexamined Patent Publication No. 2013-142073
[Patent Document 7] International Publication No. WO2015/137402
[Patent Document 8] Japanese Unexamined Patent Publication No. 2007-91652

SUMMARY OF THE INVENTION

A method in which sulfur and a basic compound are used as an oxidant of a thiol compound is an effective method capable of industrially producing a disulfide compound in an inexpensive and stable manner.

However, it was found that, in a case in which a thiol compound has a reactive functional group other than a mercapto group in the same molecule in an oxidation reaction of the thiol compound in which sulfur and a basic compound are used, a sulfur-containing ring compound is generated as a by-product due to a side reaction in the molecule, and the selection ratio of a disulfide compound which is the target compound decreases.

As a result of intensive studies, the present inventors found that, when an oxidation reaction of thiol compounds having a halohydrin structure is caused in the presence of sulfur and a specific basic compound, an oxidation reaction between mercapto groups in the thiol compounds selectively proceeds and completed the present invention.

That is, the present invention can be described as below.

[1] A process for producing a (poly) sulfide compound represented by General Formula (2), in which thiol compounds represented by General Formula (1) are reacted with each other in the presence of a basic compound represented by General Formula (4) or General Formula (5) and sulfur,

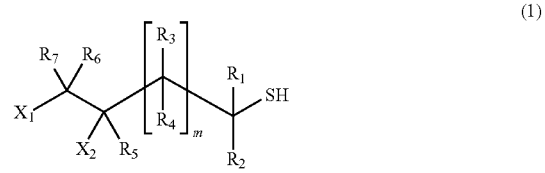

(1)

wherein, in General Formula (1), $X_1$ and $X_2$ indicate a hydroxyl group or a halogen atom, one is a hydroxyl group, and the other is a halogen atom, $R_1$ to $R_7$ may be identical to or different from each other and indicate a hydrogen atom, a C1 to C10 linear or branched alkyl group, or a substituted or unsubstituted aryl group, $R_1$ to $R_7$ may be identical to or different from each other respectively, and m indicates an integer of 0 to 2, M(SH)n (4)

wherein, in General Formula (4), M represents an alkali metal or an alkali earth metal, and n represents a valence of the alkali metal or the alkali earth metal represented by M,

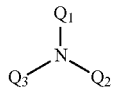
(5)

wherein, in General Formula (5), $Q_1$, $Q_2$, and $Q_3$ may be identical to or different from one another, are a hydrogen atom, a linear or branched aliphatic group having 1 to 20 carbon atoms, an alicyclic group having 3 to 20 carbon atoms, or a substituted or unsubstituted aromatic group, and these groups may include a hetero atom,

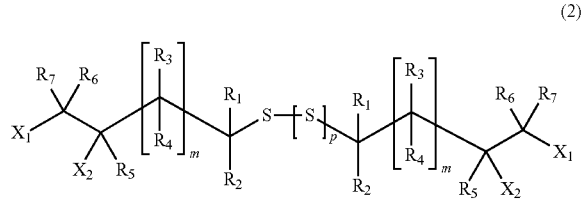
(2)

wherein, in General Formula (2), $X_1$ and $X_2$, $R_1$ to $R_7$, and m are identical to those in General Formula (1), a plurality of $X_1$ and $X_2$, $R_1$ to $R_7$, and m may be identical to or different from each other, and p indicates an integer of 0 to 4.

[2] The process for producing a (poly) sulfide compound according to [1], in which the thiol compounds are reacted at a pressure of 50 Torr to 600 Torr.

[3] The process for producing a (poly) sulfide compound according to [1] or [2], in which the halogen atom as $X_1$ or $X_2$ is a chlorine atom.

[4] The process for producing a (poly) sulfide compound according to any one of [1] to [3], in which the thiol compound represented by General Formula (1) includes a compound represented by Formula (3).

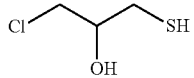
(3)

[5] The process for producing a (poly) sulfide compound according to any one of [1] to [4], in which the compound represented by General Formula (4) is sodium hydrogen sulfide.

[6] A process for producing an episulfide compound including: a step of epoxidizing the (poly) sulfide compound obtained using the process according to any one of [1] to [5] under a basic condition to obtain an epoxy compound represented by General Formula (6),

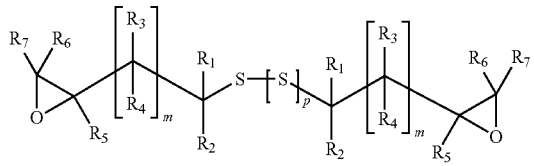
(6)

wherein, in General Formula (6), $R_1$ to $R_7$ and m are identical to those in General Formula (1), a plurality of $R_1$ to $R_7$ and m may be identical to or different from each other, and p indicates an integer of 0 to 4; and a step of reacting the epoxy compound with a sulfating agent to obtain an episulfide compound represented by General Formula (7),

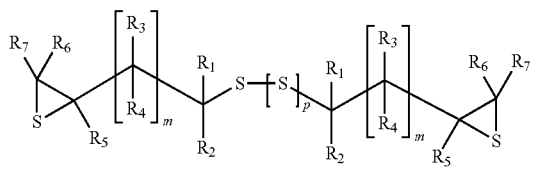
(7)

wherein, in General Formula (7), $R_1$ to $R_7$, m, and p are identical to those in General Formula (6).

[7] The process for producing an episulfide compound according to [6], in which the episulfide compound includes a compound represented by General Formula (8),

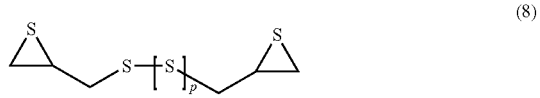
(8)

wherein, in General Formula (8), p indicates an integer of 0 to 4.

[8] The process for producing an episulfide compound according to [6] or [7], in which the episulfide compound includes a compound represented by General Formula (9).

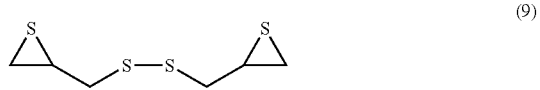
(9)

Meanwhile, in the present invention, the expression of "the thiol compounds represented by General Formula (1) are reacted with each other" refers to both an aspect in which the same kind of the thiol compounds represented by General Formula (1) are reacted with each other and an aspect in which different kinds of the thiol compounds represented by General Formula (1) are reacted with each other.

In the process of the present invention, when an oxidation reaction of thiol compounds having a halohydrin structure is caused in the presence of sulfur and a specific basic compound, an oxidation reaction between mercapto groups in the thiol compounds selectively proceeds, and it is possible to obtain a (poly) sulfide compound at a high yield. Furthermore, subsequently, when the halohydrin structure of the (poly) sulfide compound is converted to an epoxy group, and then the epoxy group is converted to an episulfide group using a sulfating agent, it is possible to obtain an episulfide compound at a high yield.

DESCRIPTION OF EMBODIMENTS

A process for producing a (poly) sulfide compound of the present invention includes a step of reacting specific thiol compounds having a halogen atom and a hydroxyl group in the molecule in the presence of a basic compound represented by General Formula (4) or General Formula (5) and sulfur to obtain a (poly)sulfide compound.

Furthermore, a process for producing an episulfide compound of the present invention includes a step of epoxidizing a (poly) sulfide compound obtained using the above-described method under a basic condition and a step of reacting an epoxy compound obtained in the above-described step with a sulfating agent to obtain an episulfide compound.

Hereinafter, an embodiment of the present invention will be described.

(Process for Producing (Poly)sulfide)

A process for producing a (poly)sulfide of the present embodiment includes a step of reacting thiol compounds represented by General Formula (1) in the presence of a basic compound represented by General Formula (4) or General Formula (5) and sulfur, thereby obtaining a (poly) sulfide compound represented by General Formula (2).

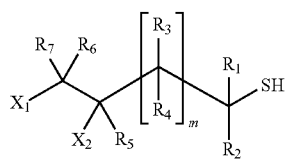

(1)

In General Formula (1), $X_1$ and $X_2$ indicate a hydroxyl group or a halogen atom, one is a hydroxyl group, and the other is a halogen atom. Examples of the halogen atom include a fluorine atom, a chlorine atom, a bromine atom, and an iodine atom, and a chlorine atom is preferred from the viewpoint of the effect of the present invention.

$R_1$ to $R_7$ may be identical to or different from each other and indicate a hydrogen atom, a C1 to C10 linear or branched alkyl group, or a substituted or unsubstituted aryl group. $R_1$ to $R_7$ may be identical to or different from each other respectively.

Examples of the C1 to C10 linear or branched alkyl group include a methyl group, an ethyl group, an n-propyl group, an isopropyl group, an n-butyl group, a sec-butyl group, a tert-butyl group, a pentyl group, a hexyl group, a heptyl group, an octyl group, a nonyl group, a decyl group, and the like.

Examples of the aryl group include aryl groups having 6 to 18 carbon atoms such as phenyl, tolyl, xylyl, biphenyl, naphthyl, anthryl, and phenanthryl.

Examples of a substituent in the substituted aryl group include an alkyl group having 1 to 10 carbon atoms, a halogen atom, a hydroxyl group, an alkoxyl group or alkylthio group having 1 to 10 carbon atoms, an amino group, and the like.

$R_1$ to $R_7$ may be identical to or different from each other and are preferably a hydrogen atom or a C1 to C10 linear or branched alkyl group, and all of them are preferably a hydrogen atom.

m indicates an integer of 0 to 2, is preferably 0 to 1, and more preferably 0.

In the present embodiment, as the thiol compound, it is possible to preferably use a compound represented by Formula (3) from the viewpoint of the effect of the present invention.

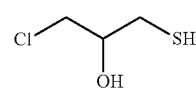

(3)

In the present embodiment, as the basic compound, it is possible to use a compound represented by General Formula (4) or a compound represented by General Formula (5).

M(SH)n (4)

In General Formula (4), M represents an alkali metal or an alkali earth metal, is preferably an alkali metal such as lithium, sodium, or potassium, and more preferably sodium. n represents a valence of the alkali metal or the alkali earth metal represented by M.

Examples of the compound represented by General Formula (4) include sodium hydrogen sulfide, potassium hydrogen sulfide, magnesium hydrogen sulfide, calcium hydrogen sulfide, and the like. In the present embodiment, sodium hydrogen sulfide is preferably used.

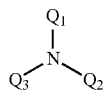

(5)

In General Formula (5), $Q_1$, $Q_2$, and $Q_3$ may be identical to or different from one another, are a hydrogen atom, a linear or branched aliphatic group having 1 to 20 carbon atoms, an alicyclic group having 3 to 20 carbon atoms, or a substituted or unsubstituted aromatic group, and these groups may include a hetero atom and are preferably a hydrogen atom, a linear or branched aliphatic group having 1 to 20 carbon atoms, or an alicyclic group having 3 to 20 carbon atoms.

Examples of the linear or branched aliphatic group having 1 to 20 carbon atoms include linear or branched alkyl groups such as a methyl group, an ethyl group, a butyl group, an isobutyl group, an octyl group, and a 2-ethylhexyl group and linear or branched alkenyl groups such as a vinyl group (ethenyl group), a butenyl group, and an octenyl group.

Examples of the alicyclic group having 3 to 20 carbon atoms include a cyclopropyl group, a cyclopentyl group, a cyclohexyl group, a cyclohexenyl group, a tetrahydropyranyl group, a tetrahydrofuranyl group, a tetrahydrothiopyranyl group, a tetrahydrothiofuranyl group, a 3-bromotetrahydropyranyl group, a 4-methoxytetrahydropyranyl group, a 4-methoxytetrahydrothiopyranyl group, a 3-tetrahydrothiophene-1,1-dioxide group, a 2-methyl-2-adamantyl group, a 2-ethyl-2-adamantyl group, and the like.

Examples of the substituted or unsubstituted aromatic group include a phenyl group, a tolyl group, a xylyl group, and the like.

In the present embodiment, $Q_1$, Q2, and Q3 are preferably identical to one another, are preferably a linear or branched aliphatic group having 1 to 20 carbon atoms, and particularly preferably an ethyl group.

Examples of the compound represented by General Formula (5) include ammonia, methylamine, ethylamine, n-propylamine, isopropylamine, n-butylamine, s-butylamine, t-butylamine, dimethylamine, diethylamine, ethylmethylamine, aniline, N-methylaniline, N-ethylaniline, trimethylamine, triethylamine, tri n-propylamine, triisopropylamine, tri n-butylamine, tri n-hexylamine, N,N-diisopropylethylamine, N,N-dimethyl-n-octadecylamine, triethylenediamine, triphenylamine, N,N-dimethylethanolamine, N,N-diethylethanolamine, triethanolamine, N,N-dimethylcyclohexylamine, N,N-diethylcyclohexylamine, N,N-dimethylbutylamine, N-methyldicyclohexylamine, N,N-dimethylaniline, N, N-diethylaniline, tetramethylethylenediamine, and the like. In the present embodiment, triethylamine is preferably used.

In a process for producing a (poly)sulfide compound of the related art, chloromercaptopropanol was reacted in the presence of sodium hydrogen carbonate and a halogen. In the method, it is necessary to use a large amount of a sodium hydrogen carbonate solution, and thus the volume efficiency is poor, and there has been room for improvement of the productivity. Furthermore, in the reaction, a hydrogen halide which is a strong acid is generated, and, separately, it is necessary to neutralize the compound, and thus steps become complicated, and there has been room for improvement of the productivity. In addition, a large amount of heat is generated during the neutralization of the hydrogen halide, and thus a cooling step or a cooling facility is required, the steps are complicated, and the production costs have been excessive.

In the present embodiment, the basic compound represented by General Formula (4) or General Formula (5) is used, and the above-described problems are solved, and thus the productivity of a (poly) sulfide compound is excellent, and it is possible to suppress the production costs.

In the present step, the thiol compounds represented by General Formula (1) are reacted with each other in the presence of the above-described basic compound and sulfur, thereby obtaining the (poly)sulfide compound represented by General Formula (2).

The present step can be carried out in a reaction solvent, and, as a reaction solvent, an aromatic solvent such as toluene, xylene, chlorobenzene, dichlorobenzene, or nitrobenzene, an aliphatic solvent such as dichloromethane, chloroform, or dichloroethane, an alcohol such as methanol, ethanol, isopropanol, butanol, methoxyethanol, ethylene glycol, or glycerin, water or the like is used. Water is particularly preferred. These solvents may be used singly, or two or more solvents may be used in a mixture form.

The amount of sulfur used is preferably 0.96 to 1.12 equivalent and more preferably 0.98 to 1.02 equivalent of the thiol compound represented by General Formula (1).

The amount of the basic compound used is preferably 1.5 to 3.5 mol %, more preferably 1.7 to 3.0 mol %, and particularly preferably 1.7 to 2.1 mol % of the thiol compound represented by General Formula (1).

The reaction temperature is preferably 3° C. to 20° C. and more preferably 5° C. to 15° C.

The reaction time is not particularly limited, but approximately 3 to 20 hours.

The reaction can be caused at the atmospheric pressure or a reduced pressure. In the case of a reduced pressure, 50 Torr to 600 Torr (6.7 kPa to 80.0 kPa) is preferred, 50 Torr to 200 Torr (6.7 kPa to 26.7 kPa) is more preferred, and 60 Torr to 80 Torr (8.0 kPa to 10.7 kPa) is particularly preferred. When the reaction is caused at a reduced pressure, a hydrogen sulfide that is generated as a by-product is discharged to the outside of the system, the inverse ratio improves, and consequently, the yield improves.

In addition, in the present step, it is also possible to carry out a reaction aspect in which the thiol compound represented by General Formula (1) is added dropwise to the above-described basic compound and sulfur or a reaction aspect in which the above-described basic compound is added dropwise to sulfur and the thiol compound represented by General Formula (1).

Due to the above-described step, an oxidation reaction between mercapto groups in the thiol compounds represented by General Formula (1) selectively proceeds, and it is possible to obtain a (poly) sulfide compound having a bishalohydrin group represented by General Formula (2) at a high yield.

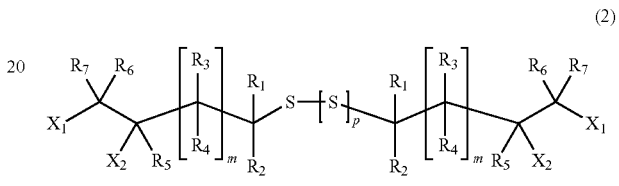

(2)

In General Formula (2), $X_1$ and $X_2$, $R_1$ to $R_7$, and m are identical to those in General Formula (1), a plurality of $X_1$ and $X_2$, $R_1$ to $R_7$, and m may be identical to or different from each other. p indicates an integer of 0 to 4.

In the present embodiment, the (poly) sulfide compound represented by General Formula (2) is preferably 1,8-dichloro-2,7-dihydroxy-4,5-dithiaoctane.

In the present embodiment, due to the above-described step, the oxidation reaction between mercapto groups in the thiol compounds represented by General Formula (1) selectively proceeds, and thus the generation of a sulfur-containing ring compound which is assumed to be a structure represented by General Formula (a) or General Formula (b) by a side reaction in the same molecule of the thiol compound is suppressed.

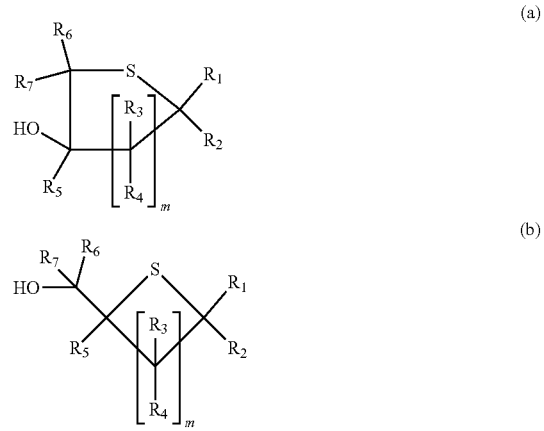

In the formulae, $R_1$ to $R_7$ and m are identical to those in General Formula (1).

In the present embodiment, the content of the sulfur-containing ring compound which is assumed to be a structure represented by General Formula (a) or General Formula (b) in a reaction liquid after the above-described step is 10 area % or less and preferably 0.1 to 5.0 area % of the (poly)sulfide compound represented by General Formula (2), and the generation of the sulfur-containing ring compound is suppressed. The content ratio is measured by high-performance liquid chromatography (HPLC).

The measurement conditions of the high-performance liquid chromatography (HPLC) are as described below.

(Measurement method)

HPLC device: SPD-10A manufactured by Shimadzu Corporation

Measurement wavelength: 210 nm

Column: YMC A-312 S-5 ODS 6 mmID×150 mm

Temperature condition: 40° C.

Mobile phase: Acetonitrile/water=⅔ (vol/vol)

Injection amount: 2 μL

Specimen adjustment: Dissolving 500 mg of the reaction liquid in 10 mL of acetonitrile In addition, the yield of the (poly) sulfide compound represented by General Formula (2) is preferably 80% to 95%.

As descried above, in the present embodiment, the generation of the sulfur-containing ring compound which is a side reactant is suppressed, and it is possible to preferably use the (poly)sulfide compound represented by General Formula (2) as a monomer for an optical material.

Furthermore, it is also possible to carry out a well-known purification step after the (poly)sulfide compound represented by General Formula (2) is obtained.

(Method for Manufacturing Episulfide)

A process for producing an episulfide compound of the present embodiment includes the following steps.

Step (i): The (poly)sulfide compound represented by General Formula (2) is epoxidized under a basic condition, and an epoxy compound represented by General Formula (6) is obtained.

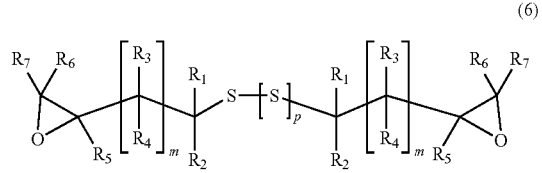

(6)

In General Formula (6), $R_1$ to $R_7$ and m are identical to those in General Formula (1), and a plurality of $R_1$ to $R_7$ and m may be identical to or different from each other. p indicates an integer of 0 to 4.

Step (ii): The epoxy compound is reacted with a sulfating agent to obtain an episulfide compound represented by General Formula (7).

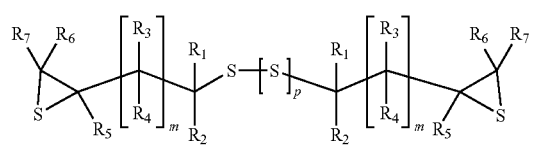

(7)

In General Formula (7), $R_1$ to $R_7$, m, and p are identical to those in General Formula (6).

The process for producing an episulfide compound of the present embodiment includes the process for producing a (poly) sulfide compound as a step, and thus, eventually, the productivity of an episulfide compound is excellent, and the production costs can be suppressed. Furthermore, for lenses that are manufactured using the episulfide compound as well, the productivity is excellent, and the production costs can be suppressed.

In addition, in the present embodiment, a (poly) sulfide compound is manufactured without using a halogen in contrast to the method of the related art, and thus the halogen content of the (poly) sulfide compound is low. In addition, the halogen content of an episulfide compound that is manufactured using the (poly) sulfide compound is also low. Therefore, in a case in which an optical material such as a lens is manufactured using the episulfide compound, the generation of a side reaction or a by-product that is derived from a halogen is suppressed, and it is also possible to obtain an optical material having an excellent quality.

These steps will be described in detail below.

Step (i)

An organic or inorganic base such as triethylamine, tributylamine, dimethylcyclohexylamine, diethylaniline, pyridine, sodium hydroxide, potassium hydroxide, magnesium hydroxide, calcium hydroxide, sodium carbonate, sodium hydrogen carbonate, potassium carbonate, sodium methylate, t-butoxy potassium, sodium monohydrogen phosphate, or sodium acetate is added to the (poly) sulfide compound represented by General Formula (2) which is obtained by reacting the thiol compounds represented by General Formula (1) in the presence of the basic compound represented by General Formula (4) or General Formula (5) and sulfur, thereby obtaining a composition including an epoxy compound.

These bases may be used singly, or two or more bases may be jointly used. The kind of the base being used is more preferably an inorganic base than an organic base, and, among inorganic bases, sodium hydroxide or potassium hydroxide is preferred.

The amount of the base used is preferably in a range of 1 equivalent to 10 equivalents and more preferably in a range of 2 equivalents to 5 equivalents of the (poly)sulfide compound.

In addition, the reaction temperature is preferably −10° C. to 60° C. and more preferably 5° C. to 30° C.

The present step can be carried out in a reaction solvent, and, as a reaction solvent, an aromatic solvent such as toluene, xylene, chlorobenzene, dichlorobenzene, or nitrobenzene, an aliphatic solvent such as dichloromethane, chloroform, or dichloroethane, an alcohol such as methanol, ethanol, isopropanol, butanol, methoxyethanol, ethylene glycol, or glycerin, water or the like is used. Water is particularly preferred. These solvents may be used singly, or two or more solvents may be used in a mixture form.

Step (ii)

The epoxy compound represented by General Formula (6) which is obtained in Step (i) is reacted with a sulfating agent to obtain an episulfide compound represented by General Formula (7).

Examples of the sulfating agent include thiocyanates such as thiourea, sodium thiocyanate, potassium thiocyanate, ammonium thiocyanate, calcium thiocyanate, and lead thiocyanate. In a case in which a thiocyanate is used, sodium thiocyanate, potassium thiocyanate, or ammonium thiocyanate is preferred, and sodium thiocyanate is more preferred.

The amount of thiourea or thiocyanate, which is the sulfating agent, used is, for example, the equivalent or more of the epoxy group, preferably in a range of 1 equivalent to 5 equivalents, and more preferably in a range of 1 equivalent to 3 equivalents. At an amount of less than 1 equivalent, the purity decreases, and, when the amount exceeds 5 equivalents, there are cases in which the method becomes economically disadvantageous.

The reaction temperature significantly varies depending on the kind of thiourea or thiocyanate and thus cannot be particularly limited; however, in a case in which thiourea is used, the reaction temperature is preferably approximately 10° C. to 30° C., and in a case in which thiocyanate is used, the reaction temperature is preferably 30° C. to 60° C.

In a case in which the episulfide compound represented by General Formula (7) is synthesized, generally, the same reaction solvent as that during the synthesis of the epoxy compound is used. For example, an aromatic solvent such as toluene, xylene, chlorobenzene, dichlorobenzene, or nitrobenzene, an aliphatic solvent such as dichloromethane, chloroform, or dichloroethane, or an alcohol such as methanol, ethanol, isopropanol, butanol, methoxyethanol, ethylene glycol, or glycerin is preferably used. These solvents may be used singly, or two or more solvents may be used in a mixture form. Unlike the case of epoxidization, in the case of thioepoxidization, there is a tendency of water decreasing the reaction rate, and thus water is not preferably used.

In the present embodiment, the episulfide compound represented by General Formula (7) is preferably an episulfide compound represented by General Formula (8) and more preferably an episulfide compound represented by General Formula (9).

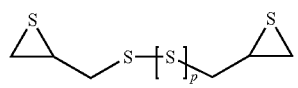
(8)

In General Formula (8), p indicates an integer of 0 to 4.

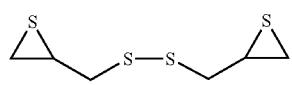
(9)

In the present embodiment, a polymerizable composition for an optical material including an episulfide compound obtained using the above-described process can be prepared using a well-known method of the related art. The polymerizable composition for an optical material is capable of including a polyisocyanate compound and/or a polythiol compound together with the obtained episulfide compound.

Furthermore, it is possible to manufacture an optical material using a well-known method of the related art from the polymerizable composition for an optical material. Specific examples of the optical material include plastic lenses, camera lenses, light-emitting diodes (LEDs), prisms, optical fibers, information-recording substrates, filters, light-emitting diodes, optical lenses for a vehicle, optical lenses for a robot, and the like. Particularly, the optical material is preferred as an optical material or an optical element such as a plastic lens, a camera lens, or a light-emitting diode.

Hitherto, the embodiment of the present invention has been described, but the embodiment is an example of the present invention, and a variety of other constitutions can be employed as long as the effects of the present invention are not impaired.

EXAMPLES

Hereinafter, the present invention will be described in more detail using examples, but the present invention is not limited thereto. In the following description, unless particularly otherwise described, "parts" and "%" are mass-based units.

[Method for Analyzing Composition of Reaction Liquid]
HPLC device: SPD-10A manufactured by Shimadzu Corporation
Measurement wavelength: 210 nm
Column: YMC A-312 S-5 ODS 6 mmID×150 mm
Temperature condition: 40° C.
Mobile phase: Acetonitrile/water=2/3 (vol/vol)
Injection amount: 2 μL
Specimen adjustment: Dissolving 500 mg of the reaction liquid in 10 mL of acetonitrile Example 1

[Synthesis of 1,8-dichloro-2,7-dihydroxy-4,5-dithiaoctane]

Distilled water (246.0 pbw), sulfur powder (14.43 pbw), and 92.3 wt % of 1-chloro-3-mercapto-2-propanol (123.5 pbw; compound: 114.0 pbw) were charged into a separable flask container and stirred while purging nitrogen gas in a gas-phase portion, and the internal temperature was set to 20° C. Next, an aqueous solution of 48 wt % of NaSH (2.73 pbw; NaSH: 1.31 pbw) was charged thereinto for one hour. After the charging, the components were stirred for three hours at an internal temperature of 20° C. The obtained reaction liquid was measured using the above-described analysis method and consequently found out to contain 1,8-dichloro-2,7-dihydroxy-4,5-dithiaoctane which was a target substance (62.5 area %).

Example 2

Distilled water (246.0 pbw), sulfur powder (14.43 pbw), and 92.3 wt % of 1-chloro-3-mercapto-2-propanol (123.5 pbw; compound: 114.0 pbw) were charged into a separable flask container and stirred while purging nitrogen gas in a gas-phase portion, and the internal temperature was set to 20° C. Next, triethylamine (2.37 pbw) was charged thereinto for one hour. After the charging, the components were stirred for three hours at an internal temperature of 20° C. The obtained reaction liquid was measured using the same method as in Example 1 and consequently found out to contain 1,8-dichloro-2,7-dihydroxy-4,5-dithiaoctane which was a target substance (71.9 area %).

Example 3

Distilled water (246.0 pbw) and sulfur powder (14.43 pbw) were charged into a separable flask container and cooled to 10° C. under stirring, and the internal pressure was reduced to 70 Torr using a pump. Next, a solution obtained by mixing 92.3 wt % of 1-chloro-3-mercapto-2-propanol (123.5 pbw; compound: 114.0 pbw) and a 48% NaSH aqueous solution (3.15 pbw; NaSH: 1.51 pbw) had been charged into a dropping funnel in advance, and the components were charged dropwise thereinto for five hours at an internal temperature of 10° C. After the dropwise charging, the components were stirred at an internal temperature of 10° C. and an internal pressure of 72 Torr to 74 Torr for 11 hours. The obtained reaction liquid was measured using the same method as in Example 1 and consequently found out to contain 1,8-dichloro-2,7-dihydroxy-4,5-dithiaoctane which was a target substance (90.6 area %).

Example 4

Distilled water (246.0 pbw), sulfur powder (14.43 pbw), and a 48% NaSH aqueous solution (3.15 pbw; NaSH: 1.51 pbw) were charged into a separable flask container and cooled to 10° C. under stirring, and the internal pressure was reduced to 70 Torr using a pump. Next, 92.3 wt % of 1-chloro-3-mercapto-2-propanol (123.5 pbw; compound: 114.0 pbw) had been charged into a dropping funnel in advance, and the components were charged dropwise thereinto for five hours at an internal temperature of 10° C. After the dropwise charging, the components were stirred at an internal temperature of 10° C. and an internal pressure of 72 Torr to 74 Torr for 11 hours. The obtained reaction liquid was measured using the same method as in Example 1 and consequently found out to contain 1,8-dichloro-2,7-dihydroxy-4,5-dithiaoctane which was a target substance (94.9 area %).

Subsequently, 1,8-dichloro-2,7-dihydroxy-4,5-dithiaoctane was separated from the reaction liquid by means of filtration, then, washed with water, and dried, thereby obtaining 1,8-dichloro-2,7-dihydroxy-4,5-dithiaoctane.

Hereinafter, the identification data of the obtained compound will be described.

$^1$H-NMR (solvent: $CDCl_3$, internal standard substance: TMS) δ: 2.64 (2H), 2.96 (4H), 3.71 (4H), 4.15 (2H)

$^{13}$C-NMR (solvent: $CDCl_3$) δ: 42.4, 48.1, 69.8

Example 5

Distilled water (246.0 pbw), sulfur powder (14.43 pbw), and triethylamine (2.73 pbw) were charged into a separable flask container and cooled to 10° C. under stirring, and the internal pressure was reduced to 70 Torr using a pump. Next, 92.3 wt % of 1-chloro-3-mercapto-2-propanol (123.5 pbw; compound: 114.0 pbw) had been charged into a dropping funnel in advance, and the components were charged dropwise thereinto for five hours at an internal temperature of 10° C. After the dropwise charging, the components were stirred at an internal temperature of 10° C. and an internal pressure of 72 Torr to 74 Torr for 11 hours. The obtained reaction liquid was measured using the same method as in Example 1 and consequently found out to contain 1,8-dichloro-2,7-dihydroxy-4,5-dithiaoctane which was a target substance (90.3 area %).

Example 6

[Synthesis of 1,8-dichloro-2,7-dihydroxy-4,5-dithiaoctane]

Distilled water (622.8 pbw), sulfur powder (36.56 pbw), and a 48% NaSH aqueous solution (0.66 pbw; NaSH: 0.32 pbw) were charged into a separable flask container and cooled to 10° C. under stirring. Next, 92.3 wt % of 1-chloro-3-mercapto-2-propanol (312.7 pbw; compound: 288.6 pbw) had been charged into a dropping funnel in advance, and the components were charged dropwise thereinto for three hours while holding the internal temperature at 10° C. After the dropwise charging, the components were stirred at 10° C. for 13 hours. During this stirring operation, the internal pressure in the reaction system was reduced to 500 Torr using a pump, reduced by 100 Torr every hour, and reduced until the internal pressure reached 100 Torr. In addition, a 48% NaSH aqueous solution (1.33 pbw; NaSH: 0.64 pbw) was additionally charged thereinto after one hour, five hours, and nine hours from the initiation of the stirring respectively. The obtained reaction liquid was measured using the same method as in Example 1 and consequently found out to contain 1,8-dichloro-2,7-dihydroxy-4,5-dithiaoctane which was a target substance (92.1 area %).

[Synthesis of Bis (2,3-epithiopropyl) disulfide]

Toluene (312.6 pbw) was charged into the obtained reaction liquid, and the internal temperature was held at 10° C. Next, an aqueous solution of 25% NaOH (474.2 pbw) was charged into a dropping funnel, and the solution was charged dropwise into the reaction liquid for two hours at 10° C. The components were stirred in a state in which the internal temperature was maintained at 10° C. for three hours from the end of the dropwise addition. The obtained reaction liquid was temporarily moved to a separating funnel, then discharging a water layer. An aqueous solution of 13% NaCl (152 pbw) was charged into the remaining toluene layer, and the pH of the reaction liquid was adjusted to 6.0 to 6.2 under stirring by adding acetic acid thereto. After the adjustment of the pH, the reaction liquid was washed at 20° C. for 15 minutes, and then a water layer was discharged. Again, an aqueous solution of 13% NaCl (152 pbw) was charged into the toluene layer and washed at 20° C. for 15 minutes, and then a water layer was discharged. The remaining toluene layer was moved to an eggplant flask, and de-toluene was conducted at 35° C. for three hours, thereby a product (200 pbw) including 94.1 wt % (1.055 mol) of bis (2,3-epoxypropyl) disulfide was obtained.

The product including bis(2,3-epoxypropyl)disulfide (198.9 pbw) was charged into a dropping funnel. Separately, a five-neck flask was prepared, acetic acid (38.5 pbw), thiourea (169.4 pbw), methanol (280 pbw), and pure water (87.5 pbw) were charged thereinto, and bis(2,3-epoxypropyl)disulfide was charged thereinto for three hours in a state of being stirred at an internal temperature of 15° C. During this dropwise addition, 88% formic acid (27.5 pbw) was charged thereinto after 30 minutes from the initiation of the dropwise addition, 88% formic acid (27.5 pbw) was charged thereinto after 90 minutes from the initiation of the dropwise addition, and 88% formic acid (27.5 pbw) was charged thereinto after 150 minutes from the initiation of the dropwise addition. After the end of the dropwise addition of the product including bis(2,3-epoxypropyl)disulfide, stirring was further continued for three hours while holding the inner temperature at 15° C. After the end of the stirring, the internal temperature was adjusted to 10° C., and methyl isobutyl ketone (400 pbw) was charged thereinto. After that, 10% ammonia water (358.5 pbw) was charged into a dropping funnel and added dropwise thereto for two hours under stirring at 10° C. After the end of the dropwise addition, the components were stirred for two hours at an internal temperature of 10° C. After the end of the stirring, the entire amount of the reaction liquid was moved to a five-neck bottomless flask and separated into an organic layer and a water layer, and the water layer was discharged. Next, an aqueous solution of pure water 13% NaCl (555.8 pbw) and 10% ammonia water (8.3 pbw) were charged thereinto, and the organic layer was washed at 20° C. to 25° C. for 15 minutes. After the end of the washing, the organic layer and the water layer were separated from each other, the water layer was discharged, then, an aqueous solution of 13% NaCl (555.8 pbw), acetic acid (6.3 pbw), and methanol (180.3 pbw) were charged thereinto, the organic layer was washed at 20° C. to 25° C. for 15 minutes, the organic layer and the water layer were separated from each other, and then the water layer was discharged. The obtained organic layer was moved to an eggplant flask, the solvent was removed at 35° C. for two hours, furthermore, topping was carried out at 35° C. for five hours, and methyl isobutyl ketone was distilled away. At this point in time, a product (213.2 pbw) including 76.8 wt % of bis (2,3-epithiopropyl) disulfide was obtained.

Next, methyl cyclohexane (1,700 pbw) was charged into a five-neck flask, the inner temperature was adjusted to 25° C., then, the entire amount of the product (213.2 pbw) including bis (2,3-epithiopropyl) disulfide was charged thereinto, and the components were stirred for one hour. After the end of the stirring, the entire amount of precipitated in-soluble substances was discharged, thereby obtaining a methyl cyclohexane solution (1,845.3 pbw).

Separately, a column tube obtained by charging the entire amount of a substance obtained by wetting silica gel (38.4 pbw) with methyl cyclohexane into a column tube was prepared. The entire amount of the methyl cyclohexane solution was passed through the column tube filled with a silica gel, thereby purifying the methyl cyclohexane solution. The purified methyl cyclohexane solution was moved to an eggplant flask, methyl cyclohexane was distilled away at 35° C. for two hours, and then, furthermore, topping was carried out at 35° C. for three hours, thereby obtaining 97.7 wt % of bis(2,3-epithiopropyl)disulfide (118.3 pbw).

Comparative Example 1

[Synthesis of 1,8-dichloro-2,7-dihydroxy-4,5-dithiaoctane]

Distilled water (246.0 pbw), sulfur powder (14.43 pbw), and 92.3 wt % of 1-chloro-3-mercapto-2-propanol (123.5 pbw; compound: 114.0 pbw) were charged into a separable flask container and stirred while purging nitrogen gas in a gas-phase portion, and the internal temperature was set to 20° C. Next, pyridine (1.85 pbw) was charged thereinto for one hour. After the charging, the components were stirred for three hours at an internal temperature of 20° C. The obtained reaction liquid was measured using the same method as in Example 1 and consequently found out to contain 1,8-dichloro-2,7-dihydroxy-4,5-dithiaoctane which was a target substance (2.6 area %).

Comparative Example 2

Distilled water (246.0 pbw), sulfur powder (14.43 pbw), and 92.3 wt % of 1-chloro-3-mercapto-2-propanol (123.5 pbw; compound: 114.0 pbw) were charged into a separable flask container and stirred while purging nitrogen gas in a gas-phase portion, and the internal temperature was set to 20° C. Next, N,N-dimethylbenzylamine (3.16 pbw) was charged thereinto for one hour. After the charging, the components were stirred for three hours at an internal temperature of 20° C. The obtained reaction liquid was measured using the same method as in Example 1 and consequently found out to contain 1,8-dichloro-2,7-dihydroxy-4,5-dithiaoctane which was a target substance (28.2 area %).

Comparative Example 3

Distilled water (246.0 pbw), sulfur powder (14.43 pbw), and 92.3 wt % of 1-chloro-3-mercapto-2-propanol (123.5 pbw; compound: 114.0 pbw) were charged into a separable flask container and stirred while purging nitrogen gas in a gas-phase portion, and the internal temperature was set to 20° C. Next, an aqueous solution of 30 wt % of sodium hydroxide (3.12 pbw; NaOH: 0.94 parts by mass) was charged thereinto for one hour. After the charging, the components were stirred for three hours at an internal temperature of 20° C. The obtained reaction liquid was measured using the same method as in Example 1 and consequently found out to contain 1,8-dichloro-2,7-dihydroxy-4,5-dithiaoctane which was a target substance (50.0 area %).

Comparative Example 4

Distilled water (246.0 pbw), sulfur powder (14.43 pbw), and 92.3 wt % of 1-chloro-3-mercapto-2-propanol (123.5 pbw; compound: 114.0 pbw) were charged into a separable flask container and stirred while purging nitrogen gas in a gas-phase portion, and the internal temperature was set to 20° C. Next, an aqueous solution of 30 wt % of sodium carbonate (8.27 pbw; Na$_2$CO$_3$: 2.48 parts by mass) was charged thereinto for one hour. After the charging, the components were stirred for three hours at an internal temperature of 20° C. The obtained reaction liquid was measured using the same method as in Example 1 and consequently found out to contain 1,8-dichloro-2,7-dihydroxy-4,5-dithiaoctane which was a target substance (54.8 area %).

TABLE 1

| | | | Example 1 | Example 2 | Example 3 | Example 4 | Example 5 | Example 6 |
|---|---|---|---|---|---|---|---|---|
| Spread liquid | Kind of basic compound | | — | — | — | Aqueous solution of 48% NaSH | Triethylamine | Aqueous solution of 48% NaSH |
| | Amount of basic compound | Parts by weight | — | — | — | 1.51 | 2.73 | 0.32 |
| | | mol %/compound A | — | — | — | 3.0 | 3.0 | 0.26 |
| | Amount of compound A | Parts by weight | 114.0 | 114.0 | — | — | — | — |
| | Amount of sulfur | Parts by weight | 14.43 | 14.43 | 14.43 | 14.43 | 14.43 | 36.56 |
| | Kind of solvent | | Water | Water | Water | Water | Water | Water |
| | Amount of solvent | Parts by weight | 246.0 | 246.0 | 246.0 | 246.0 | 246.0 | 622.8 |
| Liquid added dropwise | Kind of basic compound | | Aqueous solution of 48% NaSH | Triethylamine | Aqueous solution of 48% NaSH | — | — | Aqueous solution of 48% NaSH |
| | Amount of basic compound | Parts by weight | 1.31 | 2.37 | 1.51 | — | — | 1.92 |
| | | mol %/compound A | 2.6 | 2.6 | 3.0 | — | — | 1.49 |
| | Amount of compound A | Parts by weight | — | — | 114.0 | 114.0 | 114.0 | 288.6 |
| Oxidation reaction | Temperature | ° C. | 20 | 20 | 10 | 10 | 10 | 10 |
| | Dropwise addition time | Hr | 1 | 1 | 5 | 5 | 5 | 3 |
| | Stirring time after dropwise addition | Hr | 3 | 3 | 11 | 11 | 11 | 13 |

TABLE 1-continued

|  |  |  | Example 1 | Example 2 | Example 3 | Example 4 | Example 5 | Example 6 |
|---|---|---|---|---|---|---|---|---|
|  | Degree of pressure reduction | Torr | Normal pressure | Normal pressure | 72 to 74 (9.6 to 9.9 kPa) | 72 to 74 (9.6 to 9.9 kPa) | 72 to 74 (9.6 to 9.9 kPa) | 100 to 500 (13.3 to 66.7 kPa) |
| Measurement result | Compound A | area % | 17.5 | 12.2 | 0.5 | 0.5 | 3.6 | 2.4 |
|  | Compound B | area % | 62.5 | 71.9 | 90.6 | 94.9 | 90.3 | 92.1 |
|  | Compound C | area % | 15.0 | 15.5 | 8.0 | 1.1 | 3.7 | 4.5 |
|  | Ethanol | area % | 5.0 | 0.4 | 0.9 | 3.5 | 2.4 | 1.0 |

Compound A: 1-Chloro-3-mercapto-2-propanol
Compound B: 1,8-Dichloro-2,7-dihydroxy-4,5-dithiaoctane
Compound C: 1,9-Dichloro-2,8-dihydroxy-4,5,6-trithianonane

TABLE 2

(continue from Table 1)

|  |  |  | Comparative Example 1 | Comparative Example 2 | Comparative Example 3 | Comparative Example 4 |
|---|---|---|---|---|---|---|
| Spread liquid | Kind of basic compound |  | — | — | — | — |
|  | Amount of basic compound | Parts by weight | — | — | — | — |
|  |  | mol %/compound A | — | — | — | — |
|  | Amount of compound A | Parts by weight | 114.0 | 114.0 | 114.0 | 114.0 |
|  | Amount of sulfur | Parts by weight | 14.43 | 14.43 | 14.43 | 14.43 |
|  | Kind of solvent |  | Water | Water | Water | Water |
|  | Amount of solvent | Parts by weight | 246.0 | 246.0 | 246 | 246 |
| Liquid added dropwise | Kind of basic compound |  | Pyridine | N,N-dimethylbenzylamine | 30% NaOH | 30% $Na_2CO_3$ |
|  | Amount of basic compound | Parts by weight | 1.85 | 3.16 | 0.94 | 2.48 |
|  |  | mol %/compound A | 2.6 | 2.6 | 2.6 | 2.6 |
|  | Amount of compound A | Parts by weight | — | — | — | — |
| Oxidation reaction | Temperature | ° C. | 20 | 20 | 20 | 20 |
|  | Dropwise addition time | Hr | 1 | 1 | 1 | 1 |
|  | Stirring time after dropwise addition | Hr | 3 | 3 | 3 | 3 |
|  | Degree of pressure reduction | Torr | Normal pressure | Normal pressure | Normal pressure | Normal pressure |
| Measurement result | Compound A | area % | 31.4 | 2.3 | 14.2 | 12.4 |
|  | Compound B | area % | 2.6 | 28.2 | 50.0 | 54.8 |
|  | Compound C | area % | 54.6 | 50.0 | 15.0 | 14.8 |
|  | Ethanol | area % | 11.4 | 19.5 | 20.8 | 18.0 |

Compound A: 1-Chloro-3-mercapto-2-propanol
Compound B: 1,8-Dichloro-2,7-dihydroxy-4,5-dithiaoctane
Compound C: 1,9-Dichloro-2,8-dihydroxy-4,5,6-trithianonane The present application claims priority on the basis of Japanese Patent Application No. 2016-054906 filed on Mar. 18, 2016, the content of which is incorporated herein.

The invention claimed is:

1. A process for producing a (poly)sulfide compound represented by General Formula (2),
wherein thiol compounds represented by General Formula (1) are reacted with each other in the presence of:
(i) a basic compound represented by General Formula (4) or triethylamine and (ii) sulfur,

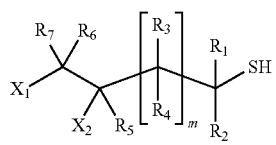

(1)

wherein, in General Formula (1), $X_1$ and $X_2$ indicate a hydroxyl group or a halogen atom, one is a hydroxyl group, and the other is a halogen atom, $R_1$ to $R_7$ may be identical to or different from each other and indicate a hydrogen atom, a $C_1$ to $C_{10}$ linear or branched alkyl group, or a substituted or unsubstituted aryl group, $R_1$ to $R_7$ may be identical to or different from each other respectively, and m indicates an integer of 0 to 2, M(SH)n (4)

wherein, in General Formula (4), M represents an alkali metal or an alkali earth metal, and n represents a valence of the alkali metal or the alkali earth metal represented by M,

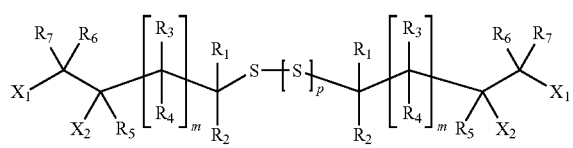

(2)

wherein, in General Formula (2), $X_1$ and $X_2$, $R_1$ to $R_7$, and m are identical to those in General Formula (1), a plurality of $X_1$ and $X_2$, $R_1$ to $R_7$, and m may be identical to or different from each other, and p indicates an integer of 0 to 4.

2. The process for producing a (poly)sulfide compound according to claim 1, wherein the thiol compounds are reacted at a pressure of 50 Torr to 600 Torr.

3. The process for producing a (poly)sulfide compound according to claim 1, wherein the halogen atom as $X_1$ or $X_2$ is a chlorine atom.

4. The process for producing a (poly)sulfide compound according to claim 1, wherein the thiol compound represented by General Formula (1) includes a compound represented by Formula (3)

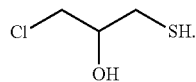
(3)

5. The process for producing a (poly)sulfide compound according to claim 1, wherein the compound represented by General Formula (4) is sodium hydrogen sulfide.

6. A process for producing an episulfide compound comprising:
a step of epoxidizing the (poly)sulfide compound obtained using the process according to claim 1 under a basic condition to obtain an epoxy compound represented by General Formula (6),

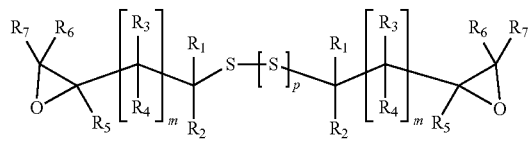
(6)

wherein, in General Formula (6), $R_1$ to $R_7$ and m are identical to those in General Formula (1), a plurality of $R_1$ to $R_7$ and m may be identical to or different from each other, and p indicates an integer of 0 to 4; and
a step of reacting the epoxy compound with a sulfating agent to obtain an episulfide compound represented by General Formula (7),

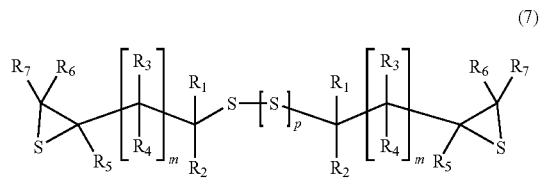
(7)

wherein, in General Formula (7), $R_1$ to $R_7$, m, and p are identical to those in General Formula (6).

7. The process for producing an episulfide compound according to claim 6, wherein the episulfide compound includes a compound represented by General Formula (8),

(8)

wherein, in General Formula (8), p indicates an integer of 0 to 4.

8. The process for producing an episulfide compound according to claim 6, wherein the episulfide compound includes a compound represented by General Formula (9)

(9)

* * * * *